US008810646B2

United States Patent
Hess

(10) Patent No.: US 8,810,646 B2
(45) Date of Patent: Aug. 19, 2014

(54) FOCUS OFFSET CONTAMINATION INSPECTION

(75) Inventor: Carl Hess, Los Altos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 324 days.

(21) Appl. No.: 13/251,975

(22) Filed: Oct. 3, 2011

(65) Prior Publication Data

US 2012/0086799 A1    Apr. 12, 2012

Related U.S. Application Data

(60) Provisional application No. 61/392,358, filed on Oct. 12, 2010, provisional application No. 61/413,471, filed on Nov. 14, 2010.

(51) Int. Cl.
*H04N 7/18* (2006.01)
*G01N 21/94* (2006.01)
*G01N 21/956* (2006.01)
*G03F 1/84* (2012.01)

(52) U.S. Cl.
CPC .............. *G01N 21/94* (2013.01); *G01N 21/956* (2013.01); *G03F 1/84* (2013.01); *G01N 2021/95676* (2013.01)
USPC ...................... 348/125; 356/237.1; 356/237.5; 382/149

(58) Field of Classification Search
None
See application file for complete search history.

(56) References Cited

U.S. PATENT DOCUMENTS

| 6,327,033 B1 * | 12/2001 | Ferguson et al. ............. 356/394 |
| 7,133,548 B2 | 11/2006 | Kenan et al. |
| 2008/0304056 A1 * | 12/2008 | Alles et al. ................. 356/237.5 |

FOREIGN PATENT DOCUMENTS

| JP | 06-308040 A | 11/1994 |
| JP | 2008-262148 A | 10/2008 |
| KR | 10-2009-007798 A | 7/2009 |

* cited by examiner

*Primary Examiner* — Christopher S Kelley
*Assistant Examiner* — Kaitlin A Retallick
(74) *Attorney, Agent, or Firm* — Suiter Swantz pc llo

(57) ABSTRACT

A system and method for detecting defects on a reticle is disclosed. The method may comprise determining a best focus setting for imaging the reticle; obtaining a first image of the reticle, the first image obtained at the best focus setting plus a predetermined offset; obtaining a second image of the reticle, the second image obtained at the best focus setting minus the predetermined offset; generating a differential image, the differential image representing a difference between the first image and the second image; and identifying a defect on the reticle based on the differential image. The method in accordance with the present disclosure may also be utilized for detecting defects on at least a portion of the reticle.

18 Claims, 6 Drawing Sheets

FOCUS OFFSET CONTAMINATION INSPECTION

CROSS-REFERENCE TO RELATED APPLICATIONS

The present application claims the benefit under 35 U.S.C. §119(e) of U.S. Provisional Application Ser. No. 61/392,358, filed Oct. 12, 2010. Said U.S. Provisional Application Ser. No. 61/392,358 is hereby incorporated by reference in its entirety.

The present application also claims the benefit under 35 U.S.C. §119(e) of U.S. Provisional Application Ser. No. 61/413,471, filed Nov. 14, 2010. Said U.S. Provisional Application Ser. No. 61/413,471 is hereby incorporated by reference in its entirety.

TECHNICAL FIELD

The disclosure generally relates to the field of contamination inspection, particularly to a system and method for detecting contamination defects on single-die or multi-die reticles.

BACKGROUND

A photomask is a plate with holes or transparencies that allow light to shine through in a defined pattern. Photomasks may be utilized for production of integrated circuit devices. For instance, a defined pattern on a photomask may be transferred to a resist arranged on a semiconductor wafer. Photomasks may be referred to as photoreticles or reticles.

Various inspection techniques may be utilized to find possible contamination (non-pattern) defects on reticles. For example, for reticles containing multiple identical dice, one of them may be utilized as a reference, which may be used to compare against another die with the same pattern in order to detect possible contaminations. However, such types of inspections may only be useful when multiple identical dice are available. If the reticle is a single die reticle, such inspection techniques are not applicable as there is no reference available.

Different inspection techniques may be utilized for reticles without repeating dice. In one example, if the design information for a given reticle is available, a high resolution scan of the reticle may be compared against the design information to detect possible contaminations. However, a high resolution scan is compute intensive and the design information may not always be available and/or accessible.

Cell-to-cell inspection is another technique that may be utilized for reticles without repeating dice. Local repeating cells (if available) may be used as a local reference to detect possible contaminations. However, cell-to-cell inspections can only over the portion of the reticle that has repeating cells of patterns (if any).

The STARlight™ inspection tool provided by KLA-Tencor Corporation of Milpitas, Calif. is another example. STARlight inspection tools may directly or indirectly use material transmission and reflection characteristics as references to detect possible contaminations. However, such type of inspection tools may be relatively slow, and may be challenged with very complex patterns having small features.

Therein lies a need for a fast and effective method for detecting contamination defects on single-die or multi-die reticles.

SUMMARY

The present disclosure is directed to a method for detecting defects on a reticle. The method may comprise determining a best focus setting for imaging the reticle; obtaining a first image of the reticle, the first image obtained at the best focus setting plus a predetermined offset; obtaining a second image of the reticle, the second image obtained at the best focus setting minus the predetermined offset; generating a differential image, the differential image representing a difference between the first image and the second image; and identifying a defect on the reticle based on the differential image. The method in accordance with the present disclosure may also be utilized for detecting defects on at least a portion of the reticle.

A further embodiment of the present disclosure is directed to an inspection system for detecting defects on a reticle. The inspection system may include an imaging device for obtaining a pair of images of at least a portion of the reticle. The first image may be obtained at the best focus setting plus a predetermined offset and the second image may be obtained at the best focus setting minus the predetermined offset. The inspection system may also include an image processor for generating a differential image for representing a difference between the first image and the second image. The inspection system may further include a user interface for presenting the differential image.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings.

Figure 1:
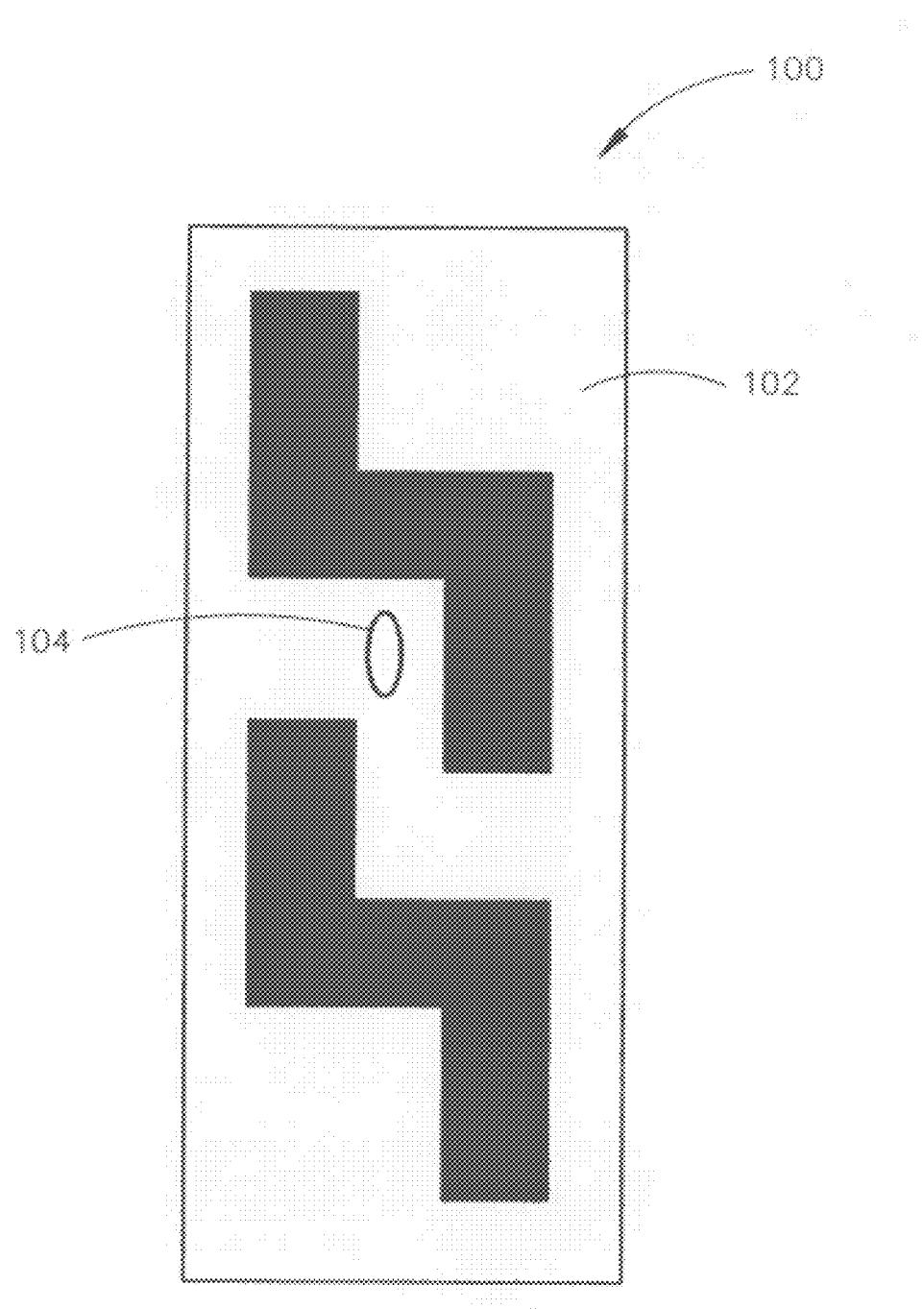
FIG. 1 is an illustration depicting the intended pattern on a local region of an exemplary reticle.

Referring to FIG. 1, an illustration depicting the intended pattern 102 on a local region of an exemplary reticle (may also be referred to as a photomask) 100 is shown. It is understood that the lines depicting the intended pattern 102 are merely for illustrative purposes and are not drawn to scale. For a 6 inches×6 inches exemplary reticle, the lines may be on the order of approximately 200 nm. It is understood that such dimensions may vary without departing from the spirit and scope of the present disclosure.

As illustrated in FIG. 1, contamination defects 104 may exist on the reticle 100. The present disclosure is directed to a system and method for detecting contamination defects on a reticle. The method in accordance with the present disclosure utilizes images of the same reticle captured/obtained at different focus settings to identify/detect the contamination defects. The method in accordance with the present disclosure does not need any reference reticle or design information that some existing inspection tools would require. In addition, the method in accordance with the present disclosure can be performed relatively quickly and can effectively handle complex patterns.

Figure 2:
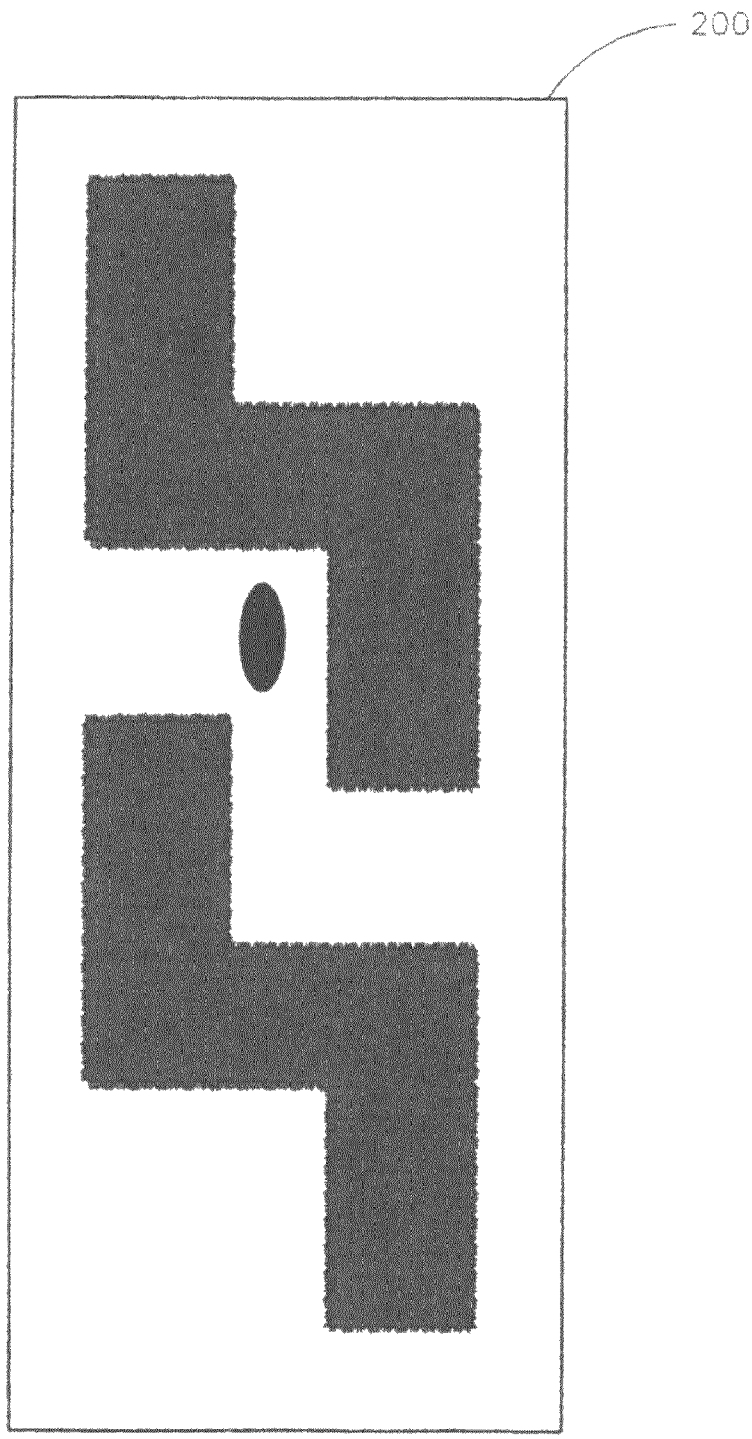
FIG. 2 is an illustration depicting a first image of the reticle obtained at the best focus setting plus a predetermined offset.
Figure 3:
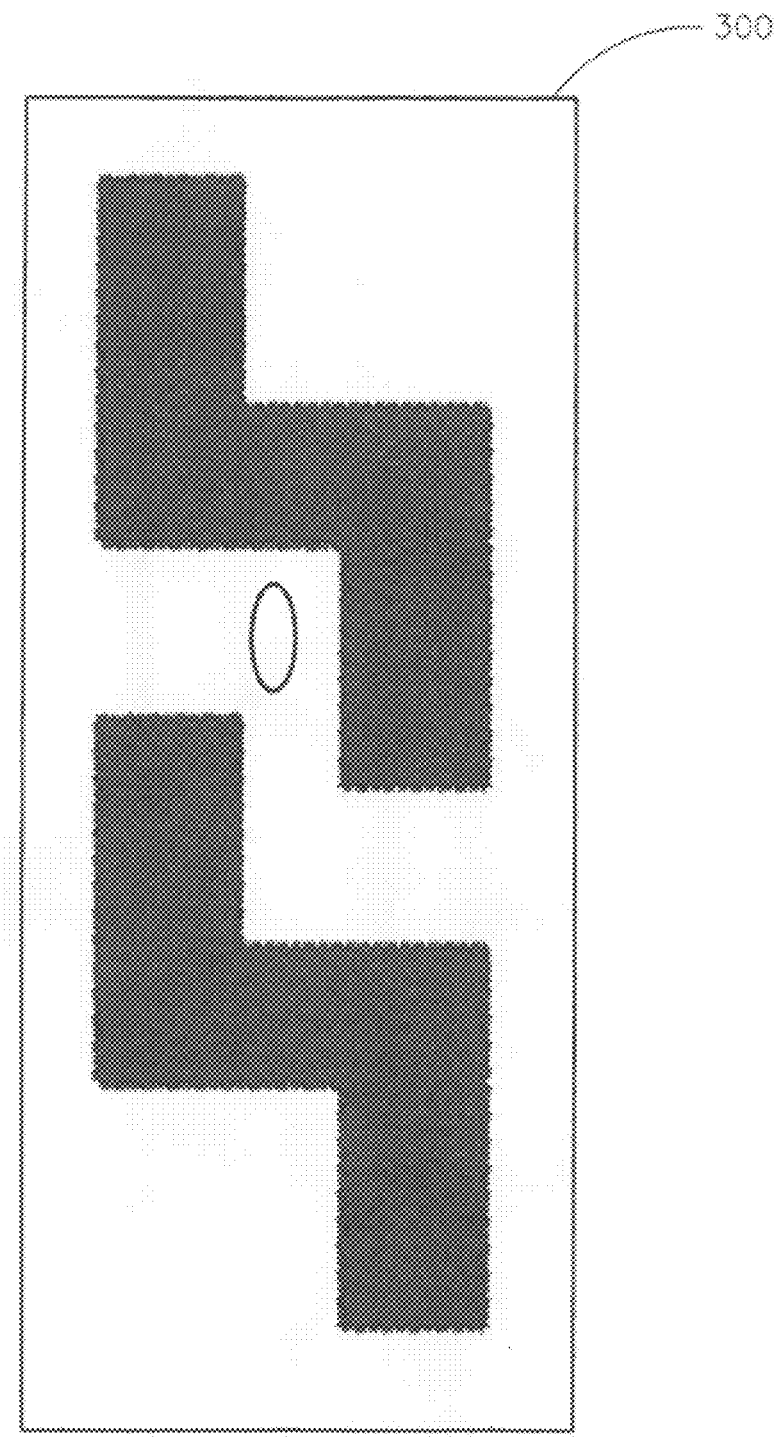
FIG. 3 is an illustration depicting a second image of the reticle obtained at the best focus setting minus the predetermined offset.

More specifically, as illustrated in FIGS. 2 and 3, two images of the reticle 100 may be obtained at different focus settings. For instance, a first image 200 may be obtained at the best focus setting plus a predetermined offset while a second image 300 may be obtained at the best focus setting minus the predetermined offset. The best focus setting is the focus setting at which the reticle 100 is optimally focused (e.g., the setting where the reticle 100 is in focus). Therefore, the two images obtained at the best focus setting plus or minus the predetermined offset may both be slightly degraded (e.g., may appear to be slightly out of focus).

The images of the generally opaque pattern 102 may degrade symmetrically in response to focus offsets. That is, the image of the intended pattern 102 obtained at the best focus setting plus the predetermined offset (i.e., focused on a plane behind the reticle 100, may also be referred to as back-focus) may degrade in substantially the same manner as the image of the intended pattern 102 obtained at the best focus setting minus the predetermined offset (i.e., focused on a plane in front of the reticle 100, may also be referred to as front-focus). Therefore, the intended pattern 102 captured on the two images, even though may appear to be slightly out of focus, may still be substantially identical in both the first image 200 and the second image 300 (it is understood that some marginal differences may exist).

On the other hand, most forms of contamination have a phase component to their transmission. Such a phase component has an asymmetrical response to focus offset (defocus). That is, for contamination defects such as defect 104 indicated in FIG. 1, the image obtained at the best focus setting plus the predetermined offset may degrade in a different manner compared to the image obtained at the best focus setting minus the predetermined offset. Therefore, defect 104 may appear differently in the first image 200 compared to the second image 300.

Figure 4:
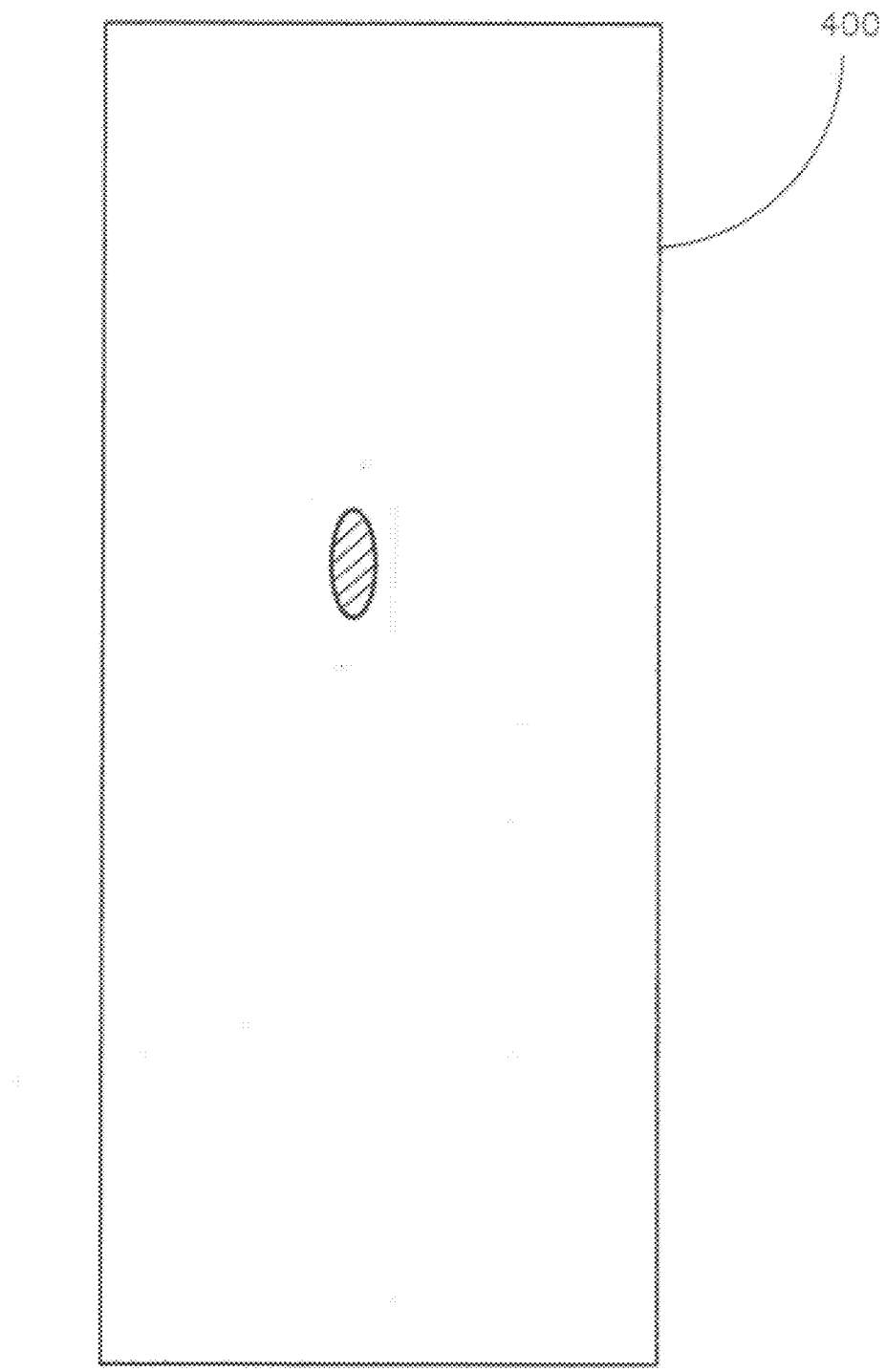
FIG. 4 is an illustration depicting a differential image representing the differences between the first image and the second image.

A differential image may be generated based on the two images obtained. As illustrated in FIG. 4, an exemplary differential image 400 may represent the difference(s) between the first image 200 and the second image 300. Since the intended pattern 102 appears to be substantially identical in both images 200 and 300, they cancel out each other in the differential image 400. Locations of any defects, on the other hand, tend to show (and may be enhanced) in the differential image 400. Such locations may then be utilized to identify/detect possible contamination defects that may exist on the reticle 100.

Figure 5:
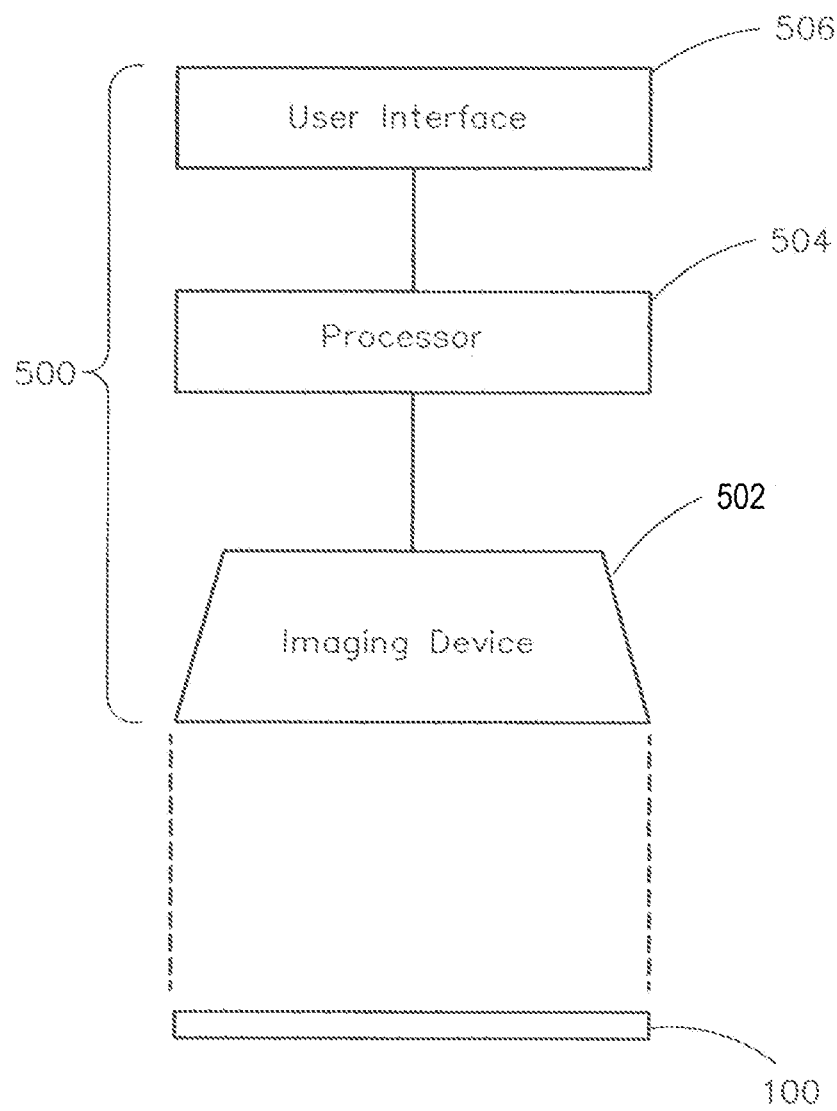
FIG. 5 is a block diagram illustrating an inspection system in accordance with the present disclosure.

FIG. 5 illustrates an inspection system 500 in accordance with the present disclosure. The inspection system 500 may include an imaging device (e.g., a scanner, a microscope or the like) 502 configured for obtaining images 200 and 300 of the reticle 100 as described above. For instance, the imaging device 502 may capture aerial images (e.g., top views) of the reticle 100 sequentially (the specific order may not matter). However, it is contemplated that imaging devices capable of simultaneously capturing images at different focus settings may also be utilized. In addition, the inspection system 500 may include more than one imaging device without departing from the spirit and scope of the present disclosure. Furthermore, the imaging device 502 may utilize software processing techniques to modify images in a manner equivalent to hardware/optical focus offset. The imaging device 502 may also be configured to obtain images of a portion/region of the reticle 100 at a time. This may be appreciated in various situation, for example, when only a portion of the reticle 100 needs to be inspected, or if the reticle 100 is too large to be inspected all at once.

The inspection system 500 may also include an image processor 504 configured for processing the obtained images. The image processor 504 may be implemented utilizing any standalone or embedded computing device (e.g., a computer, a processing unit/circuitry or the like). Upon receiving the images 200 and 300 from the imaging device 502, the image processor 504 may generate the differential image 400 that represents the difference(s) between the first image 200 and the second image 300. The differential image 400 may then be presented to a user via a user interface 506.

The image processor 504 may be further configured to provide certain diagnostic/analytical functions to identify possible contamination defects. The image processor 504 may identify the location, size and other relevant information of a possible defect based on the differential image 400. For instance, an area 402 that appears to be different from its surroundings may be identified as possible contamination defects. In addition, a threshold value may be defined to accommodate for some marginal differences that may exist between the images 200 and 300. The threshold value may be defined based on one or more of: size, contrast, color difference and/or various other factors. In this manner, only areas that differ from their surroundings by an amount greater than the threshold may be considered as possible contamination defects. The identified contamination defects may be presented to the user in addition to (e.g., as a report), in conjunction with (e.g., as markups), or in place of the differential image 400.

It is contemplated that the focus offset based inspection process in accordance with the present disclosure allows the imaging device 502 to obtain images of the reticle 100 at a relatively low resolution (e.g., at 125-nm pixel size). Therefore, the inspection process may be performed relatively quickly in comparison with conventional techniques that require higher resolution (e.g., at 55-nm pixel size) scanning. In addition, since low-resolution imaging has a much greater depth of focus than high-resolution imaging, the ability to utilize low-resolution imaging also provides for better focus control relative to the depth of focus of the imaging device 502, which may be appreciated for achieving good cancellation of images. However, it is contemplated that the specific resolution setting may vary (e.g., range between a low resolution and a high resolution) without departing from the spirit and scope of the present disclosure.

The inspection process in accordance with the present disclosure may be utilized for inspection of any single-die or multi-die reticle without using any reference die or design information. Furthermore, another advantage of the focus offset based inspection process in accordance with the present disclosure is the abilities to effectively inspect reticles with complex patterns. The differential image based inspection process does not need to resolve the fine structure of the pattern or perform modeling on the images obtained. It is the physical property of the material that creates the pair of images obtained at different focus settings with minimal processing. The use of lithographically correct illumination and imaging as well as focus offset values within the lithographic process window guarantees that the resolution and contrast will be appropriate for the reticle design.

It is contemplated that the materials used to form the intended pattern of a reticle is not required to be opaque. Certain types of partially transmissive materials such as moly silicide or the like may be utilized to form the reticles. Since such types of materials may have certain phase shifting characteristics, the images of the intended pattern taken at different focus offsets may not degrade in a perfectly symmetrical manner. Adjustments may therefore be applied to the images in order to accommodate for such phase shifting characteristics. It is understood that a specific adjustment value may be pre-computed based on the type of material, the focus offset setting as well as various other factors. It is also understood that other adjustment/correction techniques (e.g., image calibration or the like) may be utilized without departing from the spirit and scope of the present disclosure.

It is also contemplated that a calibration process may help determining the specific focus offset needed to provide appropriate cancellation between the first and the second images. For instance, a calibration process may involve taking a full series of images of a local region of a reticle, each with different focal offsets. By taking the difference of sets of images of several non-defective regions, the calibration process can determine the images with substantially different focus offsets that best cancel the intended pattern. Furthermore, the range of focus offset values to be utilized may be based on the depth of focus of the particular optical configuration. For example, the focus offset value may be up to one or two depths of focus away from best focus.

The calibration process may also determine whether the images degrade in a symmetrical manner based on the series of images taken, and whether adjustments need to be applied to the offset values. For example, the calibration process may determine a first offset value to be used as the plus offset and a second offset value to be used as the minus offset. The first and second offset values may be equal if the images degrade in a symmetrical manner. However, different offset values may be used to accommodate for possible phase shifting characteristics as described above. That is, the plus focus offset and the minus focus offset may not necessarily be the exact same magnitude.

It is further contemplated that the inspection process in accordance with the present disclosure may utilize either transmitted light or reflected light. For instance, if transmitted light is utilized, the imaging device 502 may be configured to obtain images based on light transmitted through the reticle 100. Alternatively, if reflected light is utilized, the imaging device 502 may be configured to obtain images based on light (e.g., EUV light) reflected by the reticle 100. It is understood that the specific implementation of the imaging device 502 may vary without departing from the spirit and scope of the present disclosure.

Figure 6:
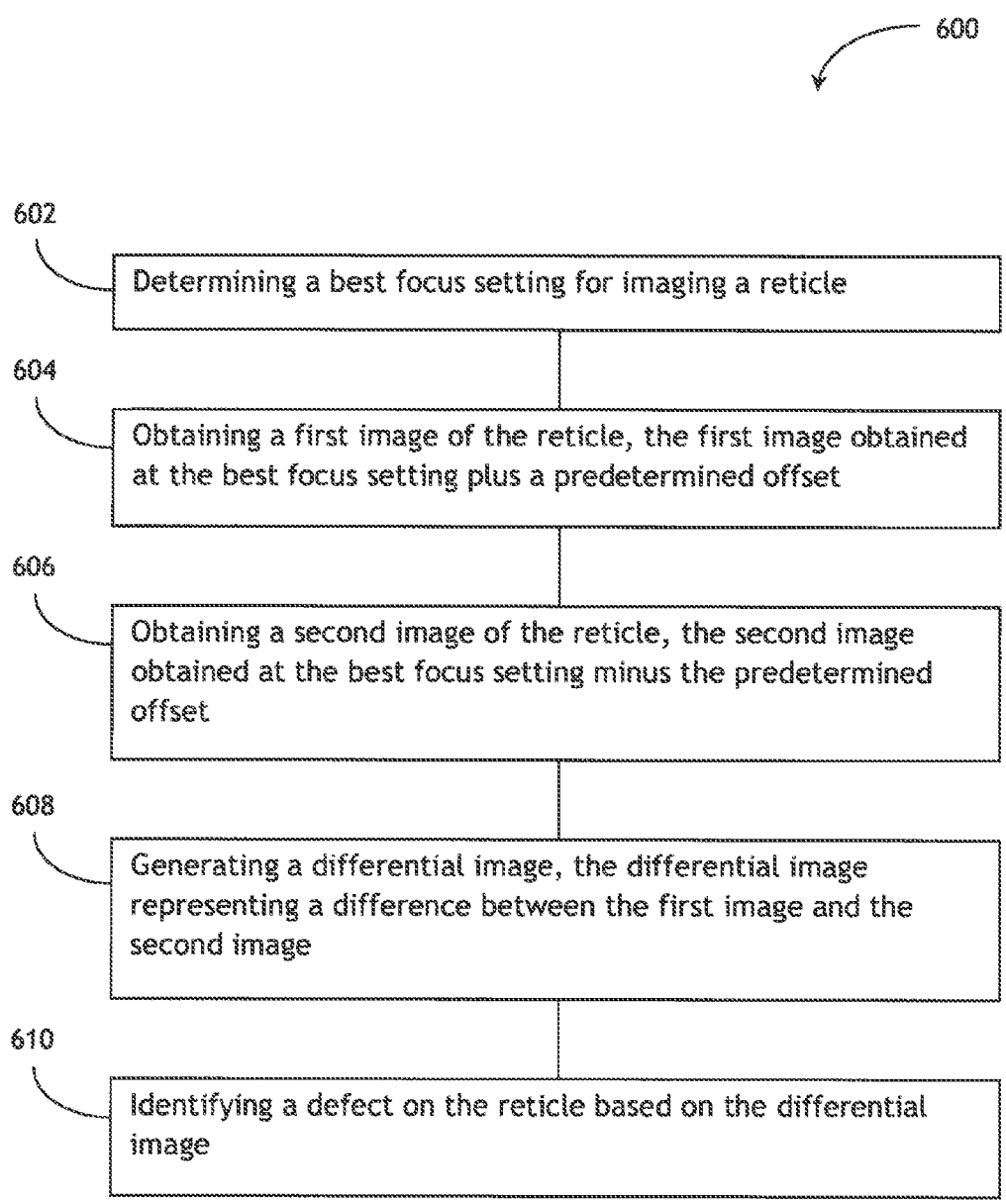
FIG. 6 is a flow diagram illustrating a method for detecting defects on a reticle in accordance with the present disclosure.

Referring to FIG. 6, a method 600 for detecting defects on a reticle is shown. Step 602 may determine the best focus setting for imaging the reticle (or a portion of the reticle). Step 604 may obtain a first image of the reticle at the best focus setting plus a predetermined offset and step 606 may obtain a second image of the reticle at the best focus setting minus the predetermined offset. Steps 604 and 606 may be performed sequentially or simultaneously. Step 608 may then generate a differential image based on the first and second image obtained. The differential image may represent the differences between the two images. Step 610 may identify potential contamination defects on the reticle based on the differential image as described above.

It is to be understood that the present disclosure may be implemented in forms of a software/firmware package. Such a package may be a computer program product which employs a computer-readable storage medium/device including stored computer code which is used to program a computer to perform the disclosed function and process of the present disclosure. The computer-readable medium may include, but is not limited to, any type of conventional floppy disk, optical disk, CD-ROM, magnetic disk, hard disk drive, magneto-optical disk, ROM, RAM, EPROM, EEPROM, magnetic or optical card, or any other suitable media for storing electronic instructions.

The methods disclosed may be implemented as sets of instructions, through a single production device, and/or through multiple production devices. Further, it is understood that the specific order or hierarchy of steps in the methods disclosed are examples of exemplary approaches. Based upon design preferences, it is understood that the specific order or hierarchy of steps in the method can be rearranged while remaining within the scope and spirit of the disclosure. The accompanying method claims present elements of the various steps in a sample order, and are not necessarily meant to be limited to the specific order or hierarchy presented.

It is believed that the system and method of the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory.

What is claimed is:

1. A method for detecting defects on a reticle, the method comprising:
   determining a best focus setting for imaging the reticle;
   taking a series of images of at least a portion of the reticle utilizing a range of different focus offset values;
   determining whether the series of images degrade in a symmetrical manner or an asymmetrical manner;
   determining a first offset and a second offset, the first offset and the second offset both being non-negative focus offsets, wherein the first offset and the second offset are equal when the series of images are determined to degrade in a symmetrical manner, and wherein the first offset and the second offset are different when the series of images are determined to degrade in an asymmetrical manner;
   obtaining a first image of at least a portion of the reticle, the first image obtained at the best focus setting plus the first offset;
   obtaining a second image of the at least a portion of the reticle, the second image obtained at the best focus setting minus the second offset;
   generating a differential image, the differential image representing a difference between the first image and the second image; and
   identifying a defect on the reticle based on the differential image.

2. The method of claim 1, wherein the first image and the second image are aerial images of the at least a portion of the reticle.

3. The method of claim 1, wherein the first image and the second image are transmitted light images.

4. The method of claim 1, wherein the first image and the second image are reflected light images.

5. The method of claim 1, wherein the first image and the second image are obtained simultaneously.

6. A method for detecting defects on a reticle, the method comprising:
   determining a best focus setting for imaging the reticle;

taking a series of images of at least a portion of the reticle utilizing a range of different focus offset values;

determining image degradation characteristics based on the series of images taken;

determining a first offset and a second offset based on the image degradation characteristics, the first offset and the second offset both being non-negative focus offsets, wherein the first offset and the second offset are different when the series of images are determined to degrade in an asymmetrical manner;

obtaining a first image of at least a portion of the reticle, the first image obtained at the best focus setting plus a first offset;

obtaining a second image of the at least a portion of the reticle, the second image obtained at the best focus setting minus a second offset;

generating a differential image, the differential image representing a difference between the first image and the second image; and identifying a defect on the reticle based on the differential image.

7. The method of claim 6, wherein the first image and the second image are aerial images of the at least a portion of the reticle.

8. The method of claim 6, wherein the first image and the second image are transmitted light images.

9. The method of claim 6, wherein the first image and the second image are reflected light images.

10. The method of claim 6, wherein the first image and the second image are obtained simultaneously.

11. The method of claim 6, wherein the first offset and the second offset are determined utilizing a calibration process prior to obtaining the first image.

12. The method of claim 6, wherein the first offset and the second offset are equal when the series of images are determined to degrade in a symmetrical manner.

13. An inspection system for detecting defects on a reticle, the inspection system comprising:

an imaging device, the imaging device configured for obtaining a first image of at least a portion of the reticle at a best focus setting plus a first offset; the imaging device further configured for obtaining a second image of the at least a portion of the reticle at the best focus setting minus a second offset;

an image processor, the image processor configured for generating a differential image for representing a difference between the first image and the second image; and a user interface, the user interface configured for presenting the differential image, wherein the first offset and the second offset are non-negative focus offsets determined based on image degradation characteristics, wherein the first offset and the second offset are equal when image degradation is symmetrical, and wherein the first offset and the second offset are different when image degradation is asymmetrical.

14. The inspection system of claim 13, wherein the image processor is further configured for determining the image degradation characteristics based on a series of images of at least a portion of the reticle taken utilizing a range of different focus offset values.

15. The inspection system of claim 13, wherein the imaging device is configured for obtaining the first image and the second image in at least one of a sequential or a simultaneous manner.

16. The inspection system of claim 13, wherein the imaging device is configured for obtaining aerial images of the at least a portion of the reticle.

17. The inspection system of claim 13, wherein the imaging device is configured for obtaining transmitted light images.

18. The inspection system of claim 13, wherein the imaging device is configured for obtaining reflected light images.

\* \* \* \* \*